US012766179B2

(12) United States Patent
Daugherty et al.

(10) Patent No.: US 12,766,179 B2
(45) Date of Patent: Oct. 20, 2026

(54) ORAL FORMULATIONS CONTAINING ENRICHED POLYPHENOLIC COMPOUNDS TOGETHER WITH A FORM OF CREATINE, A SOURCE OF CHOLINE AND TRISODIUM CITRATE

(71) Applicant: Phenolics, LLC, Omaha, NE (US)

(72) Inventors: F. Joseph Daugherty, Omaha, NE (US); Michael S. Tempesta, El Granada, CA (US)

(73) Assignee: Phenolics, LLC, Omaha, NE (US)

( * ) Notice: Subject to any disclaimer, the term of this patent is extended or adjusted under 35 U.S.C. 154(b) by 36 days.

(21) Appl. No.: 17/326,125

(22) Filed: May 20, 2021

(65) Prior Publication Data

US 2021/0361731 A1 Nov. 25, 2021

Related U.S. Application Data

(60) Provisional application No. 63/028,177, filed on May 21, 2020.

(51) Int. Cl.

| | |
|---|---|
| ***A61K 36/45*** | (2006.01) |
| ***A23L 29/00*** | (2016.01) |
| ***A23L 33/105*** | (2016.01) |
| ***A61K 9/00*** | (2006.01) |
| ***A61K 31/14*** | (2006.01) |
| ***A61K 31/155*** | (2006.01) |
| ***A61K 33/00*** | (2006.01) |

(52) U.S. Cl.

CPC ............ *A61K 36/45* (2013.01); *A23L 29/035* (2016.08); *A23L 29/045* (2016.08); *A23L 33/105* (2016.08); *A61K 9/0053* (2013.01); *A61K 31/14* (2013.01); *A61K 31/155* (2013.01); *A61K 33/00* (2013.01)

(58) Field of Classification Search

None

See application file for complete search history.

(56) References Cited

U.S. PATENT DOCUMENTS 7,306,815 B2 12/2007 Gourdin et al.

FOREIGN PATENT DOCUMENTS

| | | | | |
|---|---|---|---|---|
| DE | 102007062288 A1 * | 6/2009 | ........... A23K 1/1634 |
| JP | 2015007002 A * | 1/2015 | |
| WO | WO-2019180199 A1 * | 9/2019 | |

OTHER PUBLICATIONS

Liwei Gu et al, Concentrations of Proanthocyanidins in Common Foods and Estimations of Normal Consumption, J.Nutr., Mar. 2004, pp. 613-617, vol. 134(3).

Kazushige Yokota et al., Analysis of A-Type and B-Type Highly Polymeric Proanthocyanidins and Their Biological Activities as Nutraceuticals, J. Chem., Dec. 20, 2012, pp. 1-7, vol. 2013 article ID 352042, Hindawi Publishing Corporation.

Robert Krikorian et al., Blueberry Supplementation Improves Memory in Older Adults, J. Agric. Food Chem., 2010, pp. 3996-4000, vol. 58(7).

Carlo Abbati, Nootropic Therapy of Cerebral Aging, Advances in Therapy, 1991, pp. XX-XX, vol. 8(6), Health Communications, Inc.

Lucilla Parnetti et al., Multicentre study of I-alpha-glyceryl-phosphorylcholine vs ST200 among patients with probable senile dementia of Alzheimer's type, Drugs Aging, Mar.-Apr. 1993, pp. 159-164, vol. 3(2).

Lucilla Parnetti et al., Choline alphoscerate in cognitive decline and in acute cerebrovascular disease: an analysis of published clinical data, Mech. of Ageing and Development, 2001, pp. 2041-2055, vol. 122, Elsevier Science Ireland Ltd.

Maria De Jesus Moreno, Cognitive improvement in mild to moderate Alzheimer's dementia after treatment with the acetylcholine precursor choline alfoscerate: A multicenter, double-blind, randomized, placebo-controlled trial, Clinical Therapeutics, 2003 Jam, pp. 178-193, vol. 25(1).

Song Hee Lee et al., Late treatment with choline alfoscerate (I-alpha glycerylphosphorylcholine, α-GPC) increases hippocampal neurogenesis and provides protection against seizure-induced neuronal death and cognitive impairment. Brain Res., Jan. 1, 2017, pp. 66-76, vol. 1654(Pt A).

Chemi Nutra, AlphaSize(R) Alpha-Glyceryl Phosphoryl Choline (A-GPC) Role In Brain And Muscle Recruitment Explained, Jan. 15, 2019, Austin, TX.

Caroline Rae et al., Oral creatine monohydrate supplementation improves brain performance: a double-blind, placebo-controlled, cross-over trial, 2003, Proc. R. Soc. Lond. B., pp. 2147-2150, vol. 270.

Jeroen Van Cutsem et al., Can Creatine Combat the Mental Fatigue-associated Decrease in Visuomotor Skills?, Med Sci Sports Exerc., 2020, pp. 120-130, vol. 52(1), American College of Sports Medicine.

Olas, Berry Phenolic Antioxidants—Implications for Human Health, Frontiers in Pharmacology, Mar. 26, 2018, vol. 9, Article 78.

Keskin-Sasic et al., Total Phenolic Content and Antioxidant Capacity of Fruit Juices, Bulletin of the Chemists and Tecnologists of Bosnia and Herzegovina, 2012, 28-28, 39.

M9 Biopharmaceutics Classification System-Based Biowavers, Guidance for Industry, May 2021, Annex 1, p. 10, U.S. Department of Health and Human Services, Food and Drug Administration, Center for Drug Evaluation and Research, Center for Biologics Evaluation and Research.

* cited by examiner

*Primary Examiner* — Anand U Desai
*Assistant Examiner* — Catheryne Chen
(74) *Attorney, Agent, or Firm* — McGrath North Mullin & Kratz, PC LLO; Jeanne J. Kelley; Luke C. Holst

(57) ABSTRACT

The oral supplements of the present invention utilize phenolic compounds in combination with creatine, choline, and trisodium citrate, wherein when taken together result in enhanced cellular permeation in comparison to cellular permeation in the absence of the other compounds of the combination leading to improved brain and/or physical functioning.

19 Claims, 2 Drawing Sheets

ORAL FORMULATIONS CONTAINING ENRICHED POLYPHENOLIC COMPOUNDS TOGETHER WITH A FORM OF CREATINE, A SOURCE OF CHOLINE AND TRISODIUM CITRATE

PRIORITY

The present application claims priority of U.S. Provisional Patent Application No. 63/028,177 filed May 21, 2020, which is incorporated herein in its entirety by this reference.

FIELD OF THE INVENTION

Oral formulations including concentrated phenolic compounds, a form of creatine, a source of choline and trisodium citrate for enhanced uptake, bioavailability, improved brain, mental and/or physical functions.

BACKGROUND OF THE INVENTION

Dietary supplements include pills, capsule, tablets or liquids intended to be taken to supplement a diet. Supplements are typically extracted from food sources or synthesized wholly or in part. Supplements include nutrients such as amino acids, fiber, minerals and vitamins. Thus, supplements can address nutritional needs.

Phenolic compounds are one of the most important classes of naturally occurring compound classes found in many foods and herbs. The most important and largest class of polyphenols are known as the flavonoids, and include primarily monomers, oligomers and polymers of ellagitannins, proanthocyandins and anthocyanins, as well as many structural subclasses and naturally occurring derivatives (i.e. isoflavonoids, neoisoflavonoids, flavones, flavans, chalcones, aurones, flavanones, among others minor subclasses).

The anthocyanins and proanthocyanins are naturally occurring compounds found in many fruits, vegetables, grains, which, when extracted and/or synthesized, constitute a group of supplements available in the United States. More particularly, anthocyanins are naturally occurring compounds that are responsible for the red, purple, and blue colors of many fruits, vegetables, cereal grains, and flowers. For example, the colors of berry fruits, such as blueberries, bilberries, strawberries, raspberries, boysenberries, marionberries, cranberries, are due to many different anthocyanins. Over 300 structurally distinct anthocyanins have been identified in nature. Because anthocyanins are naturally occurring, they have attracted much interest for use as colorants for foods and beverages.

Interest in anthocyanin pigments has intensified because of their possible health benefits as dietary antioxidants. For example, anthocyanin pigments of bilberries (*Vaccinium myrtillus*) have long been used for improving visual acuity and treating circulatory disorders. There is experimental evidence that certain anthocyanins and flavonoids have anti-inflammatory properties. In addition, there are reports that orally administered anthocyanins are beneficial for treating diabetes and ulcers and may have antiviral and antimicrobial activities. The chemical basis for these desirable properties of flavonoids is believed to be related to their antioxidant capacity. Thus, the antioxidant characteristics associated with berries and other fruits and vegetables have been attributed to their anthocyanin content.

Proanthocyanidins are another class of polyphenols that are found in fruits and vegetables and, while being colorless, have antioxidant activities. As the term is commonly used, proanthocyanidins are antioxidant flavonoids with possible health benefits, found in many plant sources, including apples, bilberries, black currents, blueberries, chokeberries, cocoa/chocolate, cranberries, grapes, grapeseed, hazelnuts, pecans, pecans, pistachios, and pine bark.

Of course, the amount of proanthocyanidins in different foods varies widely, as was reported by Liwei Gu et al. in *Concentrations of Proanthocyanidins in Common Foods and Estimations of Normal Consumption*, Amer. Soc. for Nutritional Sciences, 0022-3166/04 © 2004, pp. 613-17. As reported therein, of the various fruits tested, only lowbush blueberries, cranberries, and choke berries had significant total proanthocyanidins, mostly A-type or B-type proanthocyanidins. It should be noted that while total proanthocyanidins in dried grape seed were also very abundant, from the literature these are known to be only type B or B-type proanthocyanidins.

It has also been found that the biological properties of proanthocyandins can vary. K. Yokota et al. describe in a publication entitled *Analysis of A-Type and B-Type Highly Polymeric Proanthocyanidins and Their Biological Activities as Nutraceuticals*, Journal of Chemistry, Vol. 2013, Article No. 352042, © 2013, how degradation products from extracts of seed shells of the Japanese horse chestnut, blueberry and cranberry were compared. They compared degradation products having A-type linkages with those having B-type linkages and concluded that "the isolated fractions with high molecular sizes and those more abundant in proportions of A-type linkages were found to be more effective in the inhibition of pancreatic lipase activity." They further state that their "results suggest that A-type highly polymeric proanthocyanidins are promising for the attenuation of lipid digestion as a dietary supplement."

Proanthocyanins are a class of compounds related to proanthocyanidins containing a glycoside portion. However, because the glycosidic moieties of proanthocyanins can be easily separated from the phenolic portion (such as during digestion), the in vivo activity of proanthocyanins is expected to closely track that of proanthocyanidins. Accordingly, as used herein, the term proanthocyanin is intended to encompass proanthocyanins and proanthocyanidins.

Blueberries are known to contain polyphenolic compounds, including both anthocyanins and proanthocyanins, which have antioxidant and anti-inflammatory effects. As reported by Robert Krikorian et al., *Blueberry Supplementation Improves Memory in Older Adults*, J. Agric. Food Chem, 58(7), 2010, pp. 3996-4000, anthocyanins have been associated with increased neuronal signaling in brain centers mediating memory function as well as improved glucose disposal, benefits that would be expected to mitigate neurodegeneration. Investigation of the effects of daily consumption of wild blueberry juice in a sample of nine older adults with early memory changes are as follows: at 12 weeks, improved paired associate learning ($p=0.009$) and word list recall ($p=0.04$) was observed. The findings of this study suggested that moderate-term blueberry supplementation can confer neurocognitive benefit.

In any case, due to the above characteristics and benefits of anthocyanins and proanthocyanins, much effort has been put forth towards extracting these compounds from fruits, vegetables, and other plant sources. In addition to anthocyanins, plants, fruits, and vegetables also contain other compounds such as mineral salts, common organic acids such as citric or tartaric acid, carbohydrates, flavonoid glycosides and catechins and related phenolic compounds. It is often desirable to isolate the anthocyanins and proanthocyanins from the carbohydrates and organic acids. Anthocyanins have been extracted from plants and fruits by various procedures. One extraction method of extracting anthocyanins employs sulfur dioxide. The extract is passed through an ion exchange column to adsorb the anthocyanin materials, and the adsorbed anthocyanins are eluted with acetone, alkali, or dimethyl formamide ("DMF"). Disadvantages of this process include the presence of sulfur dioxide, which interferes with adsorption of anthocyanins, thereby requiring multiple column adsorptions. Elution with alkali degrades the anthocyanins considerably, while DMF is not a recognized food additive and therefore complete removal of DMF from anthocyanins must be accomplished before the anthocyanins can be added to any food products.

Accordingly, U.S. Pat. No. 7,306,815 and related patents disclose methods for preparing compositions enriched for anthocyanins and proanthocyanins useful as nutraceuticals and pharmaceuticals. More specifically, one aspect of the invention disclosed therein provides a method of preparing compositions enriched for anthocyanins and proanthocyanins comprising: (a) extracting plants or plant parts known to contain anthocyanins with an acidified extraction solvent to form a crude extract comprising anthocyanins and extraneous compounds; (b) filtering the crude extract; contacting the filtered crude extract with a brominated polystyrene resin which adsorbs the anthocyanins but does not retain extraneous materials; and (c) eluting the anthocyanins from the brominated polystyrene resin to obtain an extract enriched for anthocyanins. These patents further provide anthocyanin-enriched compositions isolated by the methods of this invention.

Such purified plant extracts containing concentrations of anthocyanins and proanthocyanins are now widely used as nutraceuticals and pharmaceuticals. One preferred source is blueberries, classified in the Section *Cyanococcus* in the genes *Vaccinium*, with commercial sources including *Vaccinium angustifolium, V. boreale, V. caesariense, V. corybosum, V. darrowii, V. elliottii, V. formosum, V. fuscatum, V. hirsutum, V. myrsinites, V, myrtilloides, V. pallidum, V. simulatum, V. tenellum, V. virgatum*. For example, a blueberry extract available under the tradename "Micro Ingredients" is labeled as an Organic Blueberry Extract 50:1 Concentrate Powder from *Vaccinium cyanococcus*. It is labeled as sustainably grown in Canada to be used as a natural flavor for beverage, smoothie, baking and cookies, with no GMOs. The product is further described as rich in antioxidants, enzyme, flavonoids, anthocyanin, minerals (zinc, potassium, magnesium, calcium), amino acids, polyphenols, fiber and vitamins (vitamin B2, vitamin B12, vitamin C, vitamin D3, and biotin). A serving size is described as 800 mg with two servings suggested daily.

It is also noted that lignans and phenolic acids are also useful as a naturally occurring source of phenolic compounds. Phenolic acids are aromatic secondary plant metabolites, widely spread throughout the plant kingdom. Existing analytical methods for phenolic acids originated from interest in their biological roles as secondary metabolites and from their roles in food quality and their organoleptic properties. Phenolic acids or phenol carboxylic acids are types of aromatic acid compounds. Included in that class are substances containing a phenolic ring and an organic carboxylic acid function (C6-C1 skeleton). The two most important natural occurring subclasses important naturally types of phenolic acids are hydroxybenzoic acids and hydroxycinnamic acids, which are derived from non-phenolic molecules of benzoic and cinnamic acid, respectively.

Lignans and its precursors are found in a wide variety of foods, including flaxseeds, sesame seeds, legumes, whole grains, fruit, and vegetables. While most research on phytoestrogen-rich diets has focused on soy isoflavones, lignans are the principal source of dietary phytoestrogens in typical Western diet.

Choline, choline salts, including choline chloride, choline esters and phosphoryl esters, including phosphytidalcholine ("PC") are commercial forms of choline. Alpha-glycerylphosphorylcholine (L-alpha glycerylphosphoryl-choline, also known as choline alphoscerate but referred to herein as "α-GPC" or "alpha-GPC") is another choline supplement which is less widely used as a supplement, but still known. "Choline" or "a choline" as used herein is understood to include food grade or edible forms of choline and choline precursors or derivatives, including molecular choline, choline salts including choline chloride, choline esters including phosphoryl esters, including but not limited to phosphytidalcholine, and specifically α-GPC.

Alpha-GPC has a CAS Registry No. 28319-77-9, a chemical formula of C8H20NO6P, and a molar mass of 257.223 g/mol. It is a natural choline compound present in the brain. Because α-GPC is a parasympathomimetic acetylcholine precursor, it has been investigated as a possible treatment for dementias, including Alzheimer's disease. Significantly, α-GPC is able to cross the blood-brain barrier and has been shown to contribute to the cognitive recovery of patients. Intake of up to 1.2 g per day is generally considered safe.

An early study relating to α-GPC reports on a comparison of oxiracetam and choline alphoscerate in brain aging over 12 weeks is entitled *Nootropic Therapy of Cerebral Aging*, by Carlo Abbati, M D et al., ©1991 Health Communications, Inc., Advances in Therapy®, Vol. 8, No. 6, November/December 1991. The report concludes that treatment with 1 g daily of oxiracetem resulted in early improvement which was maintained during the therapy but was rapidly attenuated after discontinuation of the therapy. In contrast, it is reported that 1 g daily of choline alphoscerate evidenced a response that was slower but more sustained, with improvement maintained even eight weeks after the end of the therapy.

Other older studies relating to α-GPC include a publication by Stefano Govoni et al., entitled *Chronic Treatment with an Acetylcholine Synthesis Precursor, Alpha-Glycerylphosphorylcholine, Alters Brain Parameters Linked to Cholinergic Transmission and Passive Avoidance Behavior*, Drug Development Research, 26:439-447 (1992), Bari, Italy. This early study investigates the effect of α-GPC treatment on scopolamine-induced amnesia and acetylcholine release in rats. It was found that α-GPC was able to increase acetylcholine release in the hippocampus of the rats at a dose of 75 mg/kg i.g., with a maximum effect at 300 mg/kg i.g., and in this way is believed to lessen the effect of the scopolamine.

In a later publication, L. Parnetti et al., *Multicentre Study of l-α-glyceryl-phosphorylcholine vs ST200 among Patients with Probable Senile Dementia of Alzheimer's Type, Drugs & Aging,* 3(2): 159-64, 1993, α-GPC was compared to cytidine-diphospho-choline ("ST200") with 65 patients receiving oral 800 mg oral α-GPC in the morning and 400 mg in the afternoon, and 61 patients receiving 1000 mg ST200 in the morning and 500 mg in the afternoon. The tests were performed over a six-month period, with behavioral and neuropsychological tests conducted after prior to the study, at four months, and again at 6 months. However, intellectual and emotional impairments not only significantly improved in the α-GPC patients, the improvements were significantly better than in the ST200 patients.

In yet another publication, L. Parnetti et al., entitled *Choline alphoscerate in cognitive decline and in acute cerebrovascular disease: an analysis of published clinical data, Mechanisms of Ageing and Development,* 122 (2001) 2041-2055, related clinical data was summarized. The report concluded that based on a total of 1570 patients assessed in 10 studies involving dementia disorders, administration of choline alphoscerate improved patient clinical results with regard to cognitive symptoms of adult-onset dementia disorders.

After publication of the Parnetti publication, a study published in 2003: Dr. Jesus Moreno, *Cognitive improvement in mild to moderate Alzheimer's dementia after treatment with the acetylcholine precursor choline alfoscerate: a multicenter, double-blind, randomized, placebo-controlled trial*, Clin. Ther., January 2003, 25(1): 178-93, reported on the efficacy and tolerability of the cholinergic precursor choline alphoscerate in the treatment of cognitive impairment due to Alzheimer's disease. This study treated the non-placebo participants with 400 mg capsules of choline alphoscreate three times daily and concluded the treatment was useful for treating the cognitive symptoms of Alzheimer's disease.

More recently, Song Hee Lee et al., *Late treatment with choline alfoscerate (L-alpha glycerylphosphorylcholine, α-GPC) increased hippocampal neurogenesis and provides protection against seizure-induced neuronal death and cognitive impairment*, Brain Research, 1654 (2017) 66-76, reports that treating rats for three weeks with 250 mg/kg injections of α-GPC, three weeks after injection of a pilocarpine (to induce a seizure) resulted in improved cognitive function and increased neurogenesis.

Most recently, Chemi Nutra published an article entitled *AlphaSize® Alpha-Glyceryl Phosphoryl Choline (A-GPC) Role In Brain And Muscle Recruitment Explained*, Jan. 15, 2019, Austin, TX The publication concludes that at dosages of 100-300 mg/day, α-GPC helps maintain and improve memory, concentration, and focus, even when under stress caused by physiological and exercise induced conditions. The publication also concludes that α-GPC at 100-300 mg/day helps to increase peak power and force output during various strenuous exercises.

Alpha-GPC is now widely available as a supplement. One exemplary product is marketed by Nutricost. A suggested serving of two capsules contains a total of 600 mg of alpha-GPC. Other ingredients also include rice flour, silicon dioxide, stearic acid and vegetable magnesium stearate. According to a label on the Nutricost, Alpha GPC 300 mg, 60 Capsules bottle label, to accommodate this servicing size, the capsules are 0.875 inches long by 0.25" wide, large enough to be difficult to swallow by some individuals.

Another commercially available supplement is ALPHA GPC 50% available from Purisure in a 25 g package, with the label identifying 500 mg as constituting a single serving.

Phosphatidylcholine is available in the form of a 1200 mg single serving of a phosphatidylcholine complex containing 420 mg of phosphatidylcholine, from Double Wood Supplements, as marketed by Amazon.com. These softgels are said to be an enhanced version of sunflower and soy lecithin.

Choline DL-bitartrate powder is also available from BulkSupplements.com. A single serving size of 750 mg is labeled as containing 300 mg choline.

Another supplement, creatine, is heavily used as a dietary supplement for performance enhancement by athletes. This is because the creatine, once present in muscle tissue where it is stored as creatine phosphate, reacts with adenosine diphosphate (ADP) to restore adenosine triphosphate (ATP) levels and provide energy needed for muscle activity. By ingesting creatine, athletes are able to load their muscle tissue with higher levels of creatine phosphate and are able to better sustain muscle activity. Creatine has many commercial forms, including creatine monohydrate, creatine hydrochloride, creatine ethyl ester, buffered creatine salts and chelated creatine, including creatine magnesium chelate. However, creatine supplementation has also been studied for its effect on not just athletic performance but also with regard to mental fatigue and age-related diseases. For example, Caroline Rae et al., reported in *Oral creatine monohydrate supplementation improves brain performance: a double-blind, placebo-controlled cross-over trial*, Proc. R. Soc. Lond., B (2003) 270, 2147-50. In this study, 5 g/day of creatine supplementation for six weeks was given to vegetarian subjections. Positive results were reported for working memory and for intelligence.

More recently Jeroen Van Cutsem et al., asked *Can Creatine Combat the Mental Fatigue-associated Decrease in Visuomotor Skills*?, Med.& Sci. I Sports & Exercise, ©2019 Amer. Coll. of Sports Med. This publication touches on the possible relationship between the benefits of creatine supplement on the brain and exercise wherein the creatine is related to performance in both areas.

The foregoing functional features of each of the component classes; which each contribute to enhancing brain function and capabilities in their own separate pathway, allows for the synergistic combination of each to maximize the utility of the compositions. The advantages of the invention will be apparent from the following more particular descriptions of preferred embodiments of the invention as particularly pointed out in the appended claims.

SUMMARY OF THE INVENTION

Figure 1:
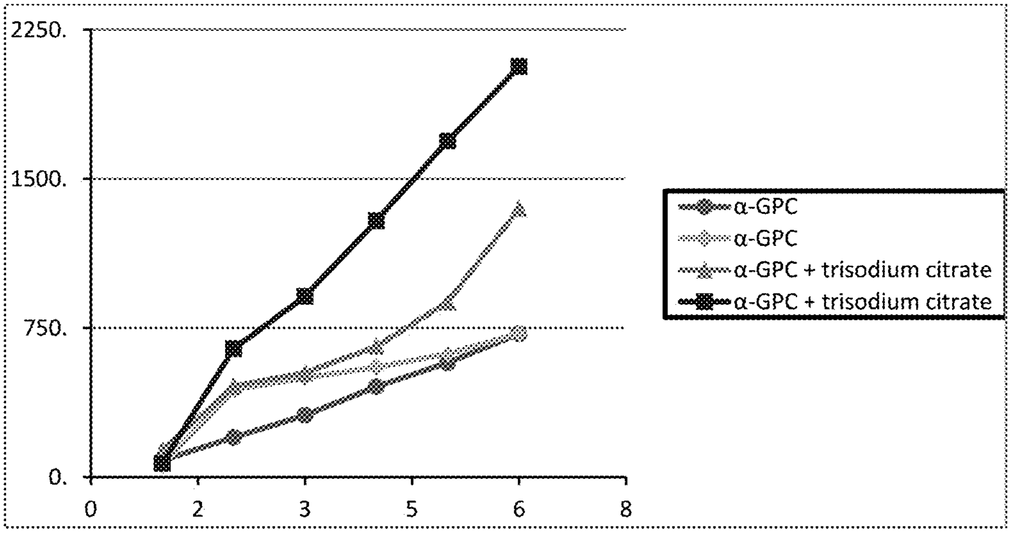
FIG. 1 illustrates the permeability of α-GPC through a Caco2 monolayer in the presence and absence of trisodium citrate incorporating study data summarized in Table 1.

The compositions and methods of the present invention utilize phenolic compounds in combination with creatine (most preferably creatine phosphate and/or creatine hydrochloride), together with choline (most preferably in the form of α-glycerolphosphorylcholine ("α-GPC") or phosphatidylcholine ("PC")), and trisodium citrate, wherein taken together in an oral supplement, the phenolic, creatine, choline and trisodium citrate components result in improved mental acuity, and/or physical cellular permeation in comparison to cellular permeation in the absence of the other compounds of the combination.

The most preferred form of choline is α-GPC whose functionality is particularly enhanced by presence of trisodium citrate. The most preferred form of creatine is disodium phosphocreatine which provides cellular phosphocreatine, the main form of creatine in the mammalian body. The most preferred phenolic compound combination is a highly purified and standardized blueberry extract whose bioavailability and functionality are also enhanced by the addition of trisodium citrate. Taken together the unique combination provides a potent and efficient formulation for use in enhancing both physical and mental functions and activities, such that unexpectedly decreased daily dosage amounts of the constituents are required as compared to prior state of the art dosages.

DETAILED DESCRIPTION OF THE INVENTION

The compositions and methods of the present invention utilize phenolic compounds in combination with creatine (most preferably creatine phosphate and/or creatine hydrochloride), together with choline (most preferably in the form of α-glycerolphosphorylcholine ("α-GPC") or phosphatidylcholine ("PC")), and trisodium citrate, wherein taken together in an oral supplement, the phenolic, creatine, choline and trisodium citrate components result in improved mental acuity, and/or physical cellular permeation in comparison to cellular permeation in the absence of the other compounds of the combination.

The most preferred form of choline is α-GPC whose functionality is particularly enhanced by presence of trisodium citrate. The most preferred form of creatine is disodium phosphocreatine which provides cellular phosphocreatine, the main form of creatine in the mammalian body. The most preferred phenolic compound combination is a highly purified and standardized blueberry extract whose bioavailability and functionality are also enhanced by the addition of trisodium citrate. Taken together the unique combination provides a potent and efficient formulation for use in enhancing both physical and mental functions and activities, such that unexpectedly decreased daily dosage amounts of the constituents are required as compared to prior state of the art dosages.

The phenolic component(s) are preferably obtained from purified plant extracts together with and compositions enriched in anthocyanins from plant materials that naturally contain anthocyanins, although synthetically derived sources are contemplated for the phenolic compounds of the present invention. When using plant extracts, the compositions of the present invention is not limited to the particular part of the plant used to prepare the phenolic component. Examples of plants and fruits that may be used in the preparation of the purified extracts of the present invention include any plant, including fruits and vegetables, that contains anthocyanins, including blueberries, bilberries, blackberries, strawberries, red currants, black currants, cranberries, cherries, raspberries, grapes, currants, elderberries, hibiscus flowers, bell peppers, red cabbage, purple corn, and violet sweet potatoes. Most colored fruits and vegetables are known to contain anthocyanins and proanthocyanidins.

The most preferred form of the creatine utilized in the compositions of the present invention is a phosphocreatine disodium salt. In these salts, the creatine is by weight approximately half of the phosphocreatine salt utilized in the present invention. Another preferred form of creatine is a dry creatine hydrochloride such as the Creatine HCl product available from BulkSupplements.com whose address is 7511 Eastgate Road, Henderson, NV 89011, which 500 g labeled product teaches a single serving size as 750 mg. Creatine monohydrate is also available from BulkSupplements.com, with product labels teaching a single serving as 2,500 mg.

However, as used herein, the term "creatine derivative" is intended to broadly encompass food grade, ingestible creatine or a creatine-based compound. In preferred embodiments of the preparations of the present invention, the creatine derivative is selected from the group consisting of creatine monohydrate, creatine hydrochloride, creatine phosphate, mixtures thereof and salts thereof. The selected compound(s) is advantageously administered orally in an amount from about 0.25 grams/day to less than 1.0 grams/day of the creatine moiety(ies)/creatine active ingredient(s) of the selected creatine derivative(s).

The compositions of the present invention are preferably made available as an encapsulated power, but may also be manufactured in any of a number of ingestible forms such as tablets, pills, powders, lozenges, elixirs, gummies, suspensions, emulsions, solutions, syrups, aerosols, ointments, soft and hard gelatin capsules. It may be possible that to also supplement a diet by utilizing the compositions of the present invention in the form of suppositories, sterile injectable solutions and sterile packaged powders.

Example 1

A most preferred embodiment of a supplement of the present invention, the following powder ingredients are blended in the following w/w percentages:

| | |
|---|---|
| Creatine Di-Sodium phosphate | 54.68% |
| Alpha GPC | 27.05% |
| Blueberry powder extract | 10.82% |
| Trisodium citrate | 6.45% |
| Magnesium stearate | 1.00% |
| Total | 100.00% |

A single dose capsule of this formulation containing about 930 mg would result in the following approximate weights of each constituent:

| | |
|---|---|
| Creatine Di-Sodium phosphate | 509 mg |
| Alpha GPC | 252 mg |
| Blueberry powder extract | 101 mg |
| Trisodium citrate | 60 mg |
| Magnesium stearate | 9 mg |
| Total | 930 mg |

Of course, in manufacturing such capsules, a single capsule run is not practicable. Assuming a single bottle of this supplement would contain 30 capsules, a 1000 bottle run preferably includes the following:

| | |
|---|---|
| Creatine di-sodium phosphate | 546.8 kg |
| Alpha GPC | 270.5 kg |
| Blueberry powder extract | 108.2 kg |
| Trisodium citrate | 64.55 kg |
| Magnesium stearate | as needed |

Described more generally, the supplement can contain approximately 500 mg creatine phosphate disodium salt (of which approximately half by weight is the creatine active ingredient), approximately 250 mg of a 50% α-GPC (L-alpha-glycerylphosphorylcholine), approximately 100 mg of a

*Vaccinium angustifolium* fruit extract standardized to approximately 30% total phenols, and approximately 60 mg of trisodium citrate. The supplement of the present invention is most preferably an admixture of dry ingredients, with the magnesium stearate, with the preferred amount of magnesium stearate in a single dose from 0 to 9 mg.

It is believed that quite possibly, substantial efficacy can be obtained with a half dosage. In this form, a single serving contains approximately 250 mg creatine active ingredient, approximately 125 mg α-GPC, approximately 50 mg total phenols and approximately 50 mg trisodium citrate. Given this total serving/daily dosage of active ingredients, the most preferred weight ratio of essential or active ingredients to each other in each serving is 10:5:2:2.

Example 2

In addition to the most preferred form, the supplement may also comprise approximately 325 mg creatine hydrochloride (of which approximately 78% by weight is the creatine active ingredient), approximately 250 mg of a 50% α-GPC, approximately 180 mg of a *Vaccinium angustifolium* fruit extract standardized to approximately 30% total phenols, and 60 mg trisodium citrate, with the magnesium stearate additive being preferred but optional. Most preferably, a single serving (which also represents the most preferred total daily dosage) contains approximately 250 mg creatine, approximately 125 mg α-GPC, approximately 50 mg total phenols and approximately 50 mg trisodium citrate.

Example 3

Another form of the supplement of the present invention may contain approximately 285 mg creatine monohydrate, approximately 250 mg of a 50% α-GPC and approximately 180 mg of a *Vaccinium angustifolium* fruit extract standardized to approximately 30% total phenols, and 50 mg trisodium citrate with the magnesium stearate additive being preferred but optional. Accordingly, in the most preferred form, a single serving (which also represents the most preferred total daily dosage) contains approximately 250 mg creatine, approximately 125 mg α-GPC, approximately 30 mg total phenols and from 25-100 mg trisodium citrate.

Example 4

In another embodiment, the supplement contains approximately 500 mg creatine phosphate disodium salt (of which approximately half by weight is the creatine active ingredient), approximately 250 mg of a 50% α-GPC and approximately 55 mg of a green tea standardized to approximately >90% total phenols, together with 100 mg trisodium citrate, with a magnesium stearate additive being preferred but optional. Accordingly, in the most preferred form, a single serving (which also represents the most preferred total daily dosage) contains approximately 250 mg creatine, approximately 125 mg α-GPC, approximately 50 mg total phenols, and from 25-100 mg trisodium citrate.

Example 5

In yet another embodiment, a supplement contains approximately 500 mg creatine phosphate disodium salt (of which approximately half by weight is the creatine active ingredient), approximately 250 mg of a 50% α-GPC and approximately 55 mg of a grape seed extract (GSE) standardized to approximately 95% total phenols, and from 10-50 mg trisodium citrate, with the magnesium stearate additive being preferred but optional. Accordingly, in this form, a single serving (which also represents the most preferred total daily dosage) contains approximately 250 mg creatine, approximately 125 mg α-GPC, from approximately 10-50 mg total phenols and from 25-100 mg trisodium citrate.

Example 6

In another formulation, the supplement of the present invention contains approximately 500 mg creatine phosphate disodium salt (of which approximately half by weight is the creatine active ingredient), approximately 150 mg of phosphatidyl choline (PC), approximately 50-180 mg of a *Vaccinium angustifolium* fruit extract standardized to approximately 30% total phenols, and 30-60 mg trisodium citrate plus optionally magnesium stearate. Accordingly, in the most preferred form, a single serving (which also represents the most preferred total daily dosage) contains approximately 250 mg creatine, approximately 150 mg PC, approximately 30-60 mg total phenols and from 25-100 mg trisodium citrate.

Example 7

Alternatively, a supplement the present invention contains approximately 500 mg creatine phosphate disodium salt (of which approximately half by weight is the creatine active ingredient), approximately 150 mg of CDP (cytidine-diphosphate choline) and approximately 50-180 mg of a *Vaccinium angustifolium* fruit extract standardized to approximately 30% total phenols, and 30-60 mg trisodium citrate, with the magnesium stearate additive being preferred but optional. Accordingly, in the most preferred form, a single serving (which also represents the most preferred total daily dosage) contains approximately 250 mg creatine, approximately 150 mg CDP, approximately 50 mg total phenols and 25-100 mg trisodium citrate.

Example 8

In yet another embodiment, the supplement contains approximately 500 mg creatine phosphate disodium salt (of which approximately half by weight is the creatine active ingredient), approximately 250 mg of a 50% α-GPC and approximately 100 mg of a turmeric extract standardized to approximately >95% total curcuminoids, together with 100 mg trisodium citrate, with a magnesium stearate additive of 0.5 mg to 10 mg being preferred but optional. Accordingly, in the most preferred form, a single serving (which also represents the most preferred total daily dosage) contains approximately 250 mg creatine, approximately 125 mg α-GPC, approximately 50 mg total phenols, and from 30-50 mg trisodium citrate. Alternatively, one could reduce the amount of the turmeric extract of which 95% curcumimoids to from less than 100 mg to 50 mg.

As indicated above, the formulations of the present invention significantly benefit from the addition of trisodium citrate. It is postulated that improvements in absorption and efficacy of the formulations of the supplements of the present invention when trisodium citrate is present may be at least partially attributed to a synergistic effect between the choline moiety (preferably derived from α-GPC) and the trisodium citrate. To evaluate this theory, the permeability of α-GPC was tested through a Caco2 monolayer in the presence and absence of trisodium citrate. Three mL of 10 mM L-α-GPC in Dulbecco's phosphate-buffered saline (known in the art as "DPBS") alone or with 10 mM trisodium citrate was added to the donor chamber of each of 3 side-by-side diffusion cells with a confluent Caco2 monolayer there between (TEER~900 Ohm*cm2). Samples were taken at 15 minute intervals for 90 minutes and replaced with fresh isotonic DPBS. Samples were taken from donor chamber at time 0 and at 90 minutes. This experiment consisted of two independent runs (runs 1 and 2). L-α-GPC was quantified using Sciex 3200 Qtrap LC/MS/MS in positive mode (257.9/104.2) using a 150 mM Phenomenex Synergi polar rp column with a mobile phase consisting of 25% methanol 75% water (v/v) with 0.1% formic acid and a flow of 0.5 ml/min.

Results from these runs were reported in terms of cumulative α-GPC measured in terms of μg/cm2 (y axis) against time in minutes (x axis). The data is summarized in Table 1 and is illustrated in FIG. 1.

TABLE 1

| | 15 min | 30 min | 45 min | 60 min | 75 min | 90 min |
|---|---|---|---|---|---|---|
| α-GPC | 84.11 | 199.54 | 310.52 | 454.48 | 574.64 | 720.21 |
| α-GPC | 59.11 | 438.47 | 499.12 | 552.54 | 620.45 | 721.50 |
| α-GPC + trisodium citrate | 135.19 | 456.27 | 524.29 | 656.83 | 879.62 | 1351.3 |
| α-GPC + trisodium citrate | 68.35 | 645.13 | 909.07 | 1288.6 | 1689.7 | 2063.9 |

These studies show that the presence of trisodium citrate significantly increases the permeation of α-GPC through a Caco2 monolayer. As a total of 30 uM α-GPC was applied to the donor chamber approximately 10% of the total α-GPC permeated in the control and between 15 and 30% permeated in the presence of trisodium citrate.

When trisodium citrate is included in the formation, preferably the trisodium citrate represents from 2% to 10% of the total weight of the formulation, more preferably 2.5% to 7.5% or even 4% to 6% of the total weight of the formulation and most preferably 3% to 5% of the total weight of the formulation.

Example 9

In addition to the most preferred embodiment of the present invention, additional additives are present in other preferred embodiments of the present invention. Other preferred embodiments containing the α-GPO, disodium phosphocreatine and phenolic extract of Example 1, but also include one or more additives selected from the group consisting of polyethylene glycol (most preferably PEG 3350), Eudraguard, α-cyclodextrin and trisodium citrate.

Example 10

In a preferred supplement of the present invention, the supplement contains approximately 100 mg of a *Vaccinium angustifolium* fruit extract standardized to approximately 30% total phenols and either approximately 500 mg creatine phosphate disodium salt (of which approximately half by weight is the creatine active ingredient) or approximately 250 mg of a 50% α-GPC, together with from 20-100 mg trisodium citrate. In one of these formulations, a single serving contains approximately 50 mg total phenols and either approximately 250 mg creatine or approximately 125 mg α-GPC.

Example 11

In other forms of the supplement of the present invention the supplement contains from 100 to 750 mg of creatine phosphate disodium salt, from 50 mg to 500 mg of a 50% α-GPC, from 50 to 250 mg of a *Vaccinium angustifolium* fruit extract standardized to approximately 30% total phenols, and approximately 0 to 200 mg of trisodium citrate. It is believed that the amount of the trisodium citrate may be decreased in formulations such as these in that the creatine source may contribute significant sodium for the purpose of enhancing activity of the resulting combination.

Example 12

In addition to the most preferred embodiment of the present invention, additional additives are present in other preferred embodiments of the present invention. Other preferred embodiments containing the α-GPO, disodium phosphocreatine, phenolic extract and trisodium citrate of Example 1 (or alternatively other creatine derivative described herein) but also include one or more additives selected from the group consisting of polyethylene glycol (most preferably PEG 3350), Eudraguard, and alpha-cyclodextrin. Preferably, these additives do not constitute more than 2% of the essential or active ingredients or 0-20 mg of a single dose.

More generally, the preferred supplements of the present invention include one or more plant extracts enriched in polyphenols. Plant extracts are most preferably extracts selected from the group consisting of bilberries, blueberries, cranberries, chokeberries, strawberries, black currents, grapes, grape seeds, plums, sorghum, pinto beans, red beans, kidney beans, hazelnuts, pecans, pistachios, teas and cinnamon. Such extracts enriched in polyphenols may, in their simplest form, comprise juices in which the water content of is all, mostly or partially evaporated. More preferred plant extracts are processed in a way which includes multiple steps which may include one or more of the following steps: evaporation, filtration, centrifugation, column chromatography separation, liquid-liquid separation and size exclusion chromatography. In any case, the most preferred phenolic compounds include anthocyanins and/or proanthocyanins (type A and/or type B) and related phenolic compounds, as well one or more compounds selected from the group consisting of creatine (and/or creatine derivatives) and choline (including α-GPC). The creatine compounds in these supplements are most preferably creatine phosphate and salts.

The preferred choline in the supplements of the present invention comprise α-GPC. Trisodium citrate is also a most preferable additive and may be included in the supplements of the present invention.

The most preferred supplements of the present invention comprise a plant extract comprising a blueberry extract containing at least 30% total phenols, wherein a daily dosage of the supplement comprises 100-300 mg of 50% α-GPC, 300-750 mg of disodium phosphocreatine, and 100-250 mg of the blueberry extract. These supplements also may include 50-300 mg trisodium citrate.

In another series of experiments, the permeability of α-GPC through a Caco2 monolayer was measured to determine whether the presence of a blueberry-based polyphenol extract affected permeability. It was found that the presence of a blueberry polyphenol extract does not significantly change the permeation of α-GPC through a Caco2 monolayer. Additionally, it was determined that the presence of α-GPC did not significantly change the permeation for the blueberry polyphenols through the Caco2 monolayer.

Figure 2:
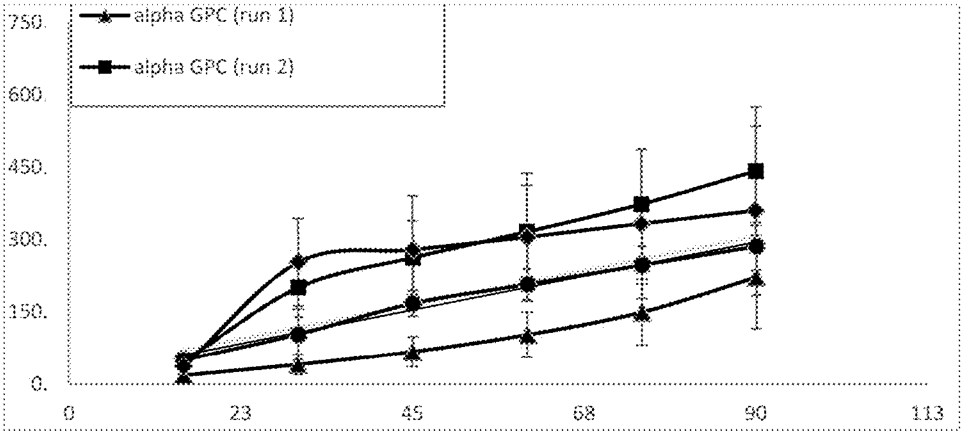
FIG. 2 illustrates the permeability of α-GPC through a Caco2 monolayer in the presence and absence of blueberry extract incorporating study data summarized in Table 2.
Figure 3:
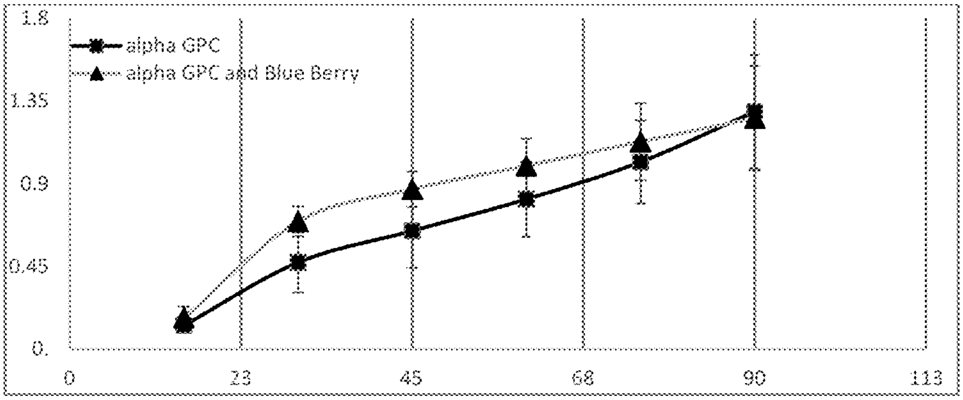
FIG. 3 illustrates the permeability of α-GPC through a Caco2 monolayer in the presence and absence of blueberry extract incorporating study data summarized in Table 3.

More particularly, donor GPC concentrations were reduced to 5 mM. Three ml of 5 mM I-α-GPC in Dulbecco's phosphate-buffered saline (DPBS) alone or with 1 mg/ml blueberry polyphenol extract was added to donor chambers of each of 3 side by side diffusion cells with a confluent Caco2 monolayer between (TEER~900 Ohm*cm2). Samples were taken at 15 minute intervals for 90 minutes and replaced with fresh isotonic DPBS. Samples were taken from donor chamber at time 0 and at 90 minutes. This experiment consisted of two independent runs (as identified below as run 1 and run 2). Alpha GPC was quantified using Sciex 3200 Qtrap LC/MS/MS in positive mode (257.9/104.2) using a 150 mM Phenomenex Synergi polar rp column with a mobile phase consisting of 25% methanol 75% water (v/v) with 0.1% formic acid and a flow of 0.5 ml/min. The data from the runs is summarized in Table 2, illustrated in FIG. 2 (Total Alpha GPC permeability through a Caco2 monolayer) and averaged below in Table 3. The averaged data is illustrated in FIG. 3. In each of the graphs, the vertical axis units are cumulative L-α-GPC in μg/cm2 and the horizontal axis units are minutes.

TABLE 2

| | 15 min | 30 min | 45 min | 60 min | 75 min | 90 min |
|---|---|---|---|---|---|---|
| (1) αGPC | 18.75 | 41.37 | 67.92 | 103.2 | 150.0 | 222.4 |
| (2) αGPC | 47.16 | 200.9 | 262.8 | 316.1 | 373.3 | 442.1 |
| (1) αGPC + blueberry | 50.76 | 104.0 | 168.3 | 207.5 | 247.3 | 286.4 |
| (2) αGPC + blueberry | 37.03 | 253.1 | 279.0 | 305.2 | 333.0 | 360.1 |

TABLE 3

| | 15 min | 30 min | 45 min | 60 min | 75 min | 90 min |
|---|---|---|---|---|---|---|
| αGPC | 0.128 | 0.471 | 0.643 | 0.815 | 1.017 | 1.292 |
| αGPC + blueberry | 0.171 | 0.694 | 0.870 | 0.997 | 1.128 | 1.256 |

Figure 4:
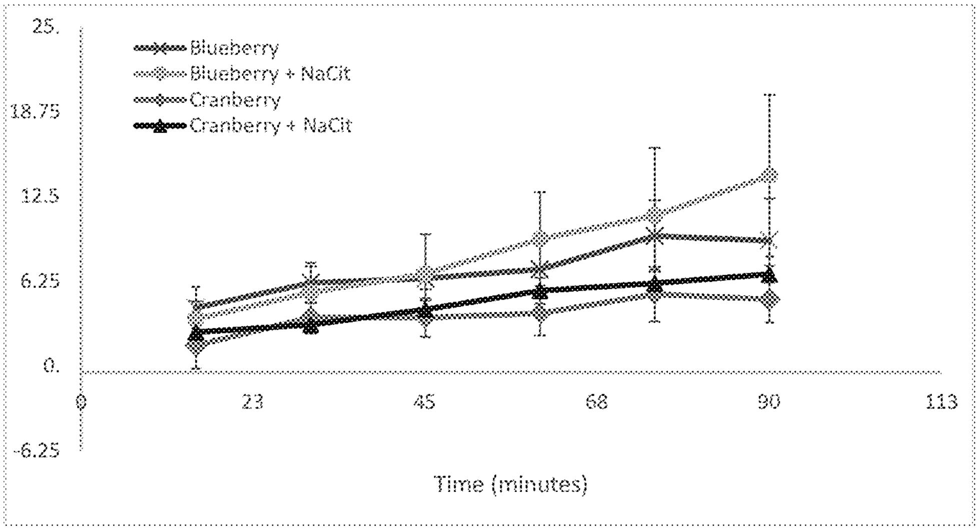
FIG. 4 illustrates cumulative polyphenol permeation through a Caco2 membrane based on study data summarized in Table 4.

It is noted that not all polyphenolic extracts are enhanced as effectively as the concentrated blueberry extract used in the preferred embodiments described herein. In experiments conducted to compare the effect of trisodium citrate on a blueberry extract and on a cranberry extract, tests conducted using the Caco2 monolayer as described above showed a modest improvement of the cranberry extract to which the trisodium citrate was added, but this effect was measurably less than the effect of the trisodium citrate on permeation blueberry extract. It is postulated that the enhancement effect may be unusually superior due to the unique polyphenol size distribution in the blueberry extract, in which there are significant numbers of smaller polyphenol molecules. Data was collected and averaged at 15, 30, 45, 60, 75 and 90 minutes, and is summarized in Table 4. FIG. 4 illustrates this data which taken as a whole, represents the cumulative polyphenol permeation through a Caco2 membrane. The vertical axis of FIG. 4 represents cumulative polyphenols in ug propyl galate equivalents. The horizontal axis represents time in minutes.

TABLE 4

| | Blueberry | Blueberry + Trisodium Citrate | Cranberry | Cranberry + Trisodium Citrate |
|---|---|---|---|---|
| 15 min | 4.274 | 3.439 | 1.490 | 2.464 |
| 30 min | 6.101 | 5.404 | 3.548 | 3.014 |
| 45 min | 6.442 | 6.767 | 3.541 | 4.144 |
| 60 min | 7.108 | 9.335 | 3.859 | 5.530 |
| 75 min | 9.560 | 11.069 | 5.268 | 6.080 |
| 90 min | 9.229 | 14.009 | 4.889 | 6.746 |

A preferred formulation of the supplement of the present invention containing 500 mg of disodium phophocreatine, 250 mg of α-glycerol phosphocholine, 200 mg of blueberry extract and 60 mg of trisodium citrate was provided as a single oral dose taken in the morning to volunteers. The volunteers spanned an age of 40 to late 80's in age, with an approximate median age of 60 years old. Two of the individuals were in their 80s and both suffered from age-related cognitive and physical decline with mild to moderate dementia. The elder man was taking required medical treatment for onset Alzheimer's disease. After the first two weeks of daily use, each volunteer exhibited remarkable improvement in daily cognitive function, i.e., alertness, conversational skills, problem solving, improvement in the daily routine for personal care, and improved physical activity. In particular, the two elderly volunteers exhibited marked improvement in the ability to be up and around, contributing to conversations, as well as daily dressing and self-care, which required substantially less time.

Accordingly, a method of promoting health in individual persons, includes the steps of administering the oral supplements to a human being is contemplated by formulations and combinations described herein, it being understood that certain combinations will prove optimum. Furthermore, it is also contemplated that oral administration of the oral supplements of the present invention may find utility when administered to other mammals such as dogs and cats, provided the amounts of the individual doses are adjusted appropriately.

Furthermore, depending upon the size/body mass/age of the individual taking the oral supplements of the present invention, fractional doses of these oral doses may be appropriate. So, for example, a half dose of any of the examples and ranges described above may be taken each day if desired. Also by way of example, two half doses or other fractional doses each day may be deemed appropriate if the size of the full dose described herein in the examples and ranges above if difficult for an individual to swallow.

In addition to dosage size variations of the examples and ranges described above, the inventors hereof believe that unexpected improvements in physical, cognitive, and other mental health may be achieved even in the absence of the trisodium citrate, although such improvements will be more modest than those achieved with the oral dietary supplement of the present invention comprising a plant extract enriched in polyphenols, a creatine derivative, a choline, and trisodium citrate. Accordingly, the invention described herein also contemplates an oral dietary supplement comprising a plant extract enriched in polyphenols, a creatine derivative and a choline. The relative weights and weight ranges of dosages for this aspect of the present invention are in the many combinations specified above, but omitting the trisodium citrate.

In summary, the oral dietary supplement of the present invention includes a plant extract enriched in polyphenols in which the plant extract enriched in polyphenols is extracted and selected from the group consisting of polyphenol-containing fruits, fibrous edibles, beans, nuts, spices, teas, vegetables, flowers and grasses and the polyphenols are selected from the group consisting of monomers, dimers, trimers, oligomers and polymers, together with a creatine derivative, a form of choline, and trisodium citrate.

Preferably the oral dietary supplements of the present invention includes polyphenols selected from the group consisting of anthocyanins, phenolic acids, lignans, flavonoids and proanthocyanins, the creatine derivative is selected from the group of creatine itself, creatine monohydrate, creatine salts, creatine esters, creatine phosphoryl esters and their salts, and creatine chelates, and the choline is a choline derivative selected from the group consisting of choline itself, choline salts, choline esters and choline phosphoryl esters.

The plants from which the plant extracts enriched in polyphenols are preferably extracted from one or more of the following: acai, aronia, bilberries, blueberries, cranberries, chokeberries, coffee berries, currants, red currents, black currents, black raspberries, elderberries, grapes, mangos, marionberries, peaches, pomegranate, plums, prunes, raspberries and strawberries, the fibrous edibles are selected from the group consisting of sorghum, radish, potato, rutabaga and turnip, the beans are selected from the group consisting of pinto beans, red beans and kidney beans, the nuts are selected from the group consisting of hazelnuts, pecans, pistachios, and walnuts, the spices are selected from the group consisting of cinnamon, curcumin, turmeric and pepper seeds, and the vegetables are selected from the group consisting of artichokes, asparagus, carrots, endives, olives, onions, spinach, shallots, red lettuce, and pepper.

Preferably, fruits are the source of the plant extracts used in the present and the preferred fruits acai, aronia, bilberries, blueberries, cranberries, chokeberries, coffee berries, black currants, black raspberries, elderberries, grapes, peaches, mangosteen, pomegranate, plums, prunes, raspberries and strawberries.

In the present invention, creatine itself and salts thereof may be used. Alternatively, creatine hydrochloride may be used. Also, α-GPC a preferred form of the choline used in formulations of the present invention. Furthermore, polyethylene glycol may also be incorporated in the formulations of the present invention.

Example 13

In order to more fully understand the effects of the formulations within the invention, an ad hoc clinical dosing evaluation was conducted over the course of several months in 24 human subjects. In this evaluation, three different formulation dosing levels were sampled and tried by the subjects for between 1 day and up to 30 days. The formulations were as follows:

| | α-GPC | Phospho-Creatine | Blueberry Extract | Tri Sodium Citrate |
|---|---|---|---|---|
| Low Dose | 63 mg | 250 mg | 50 mg | 30 mg |
| Mid Dose | 125 mg | 500 mg | 100 mg | 60 mg |
| High Dose | 250 mg | 500 mg | 100 mg | 60 mg |

Most of the participants in this ad hoc study reported one or more of the following positive results (a) improvement in short-term memory, as reflected in staying on task without fewer lapses of memory, (b) improvement in long-term memory, (c) better sleep as described as more restful with fewer interruptions each night, (d) noticeable improvements in daily energy, allowing for the lessening the need of stimulants via coffee or tea with caffeine.

Not everyone experienced precisely the same effect, and some did not see much difference between the different doses consumed. For those consuming the highest dose there was a greater differential of effect, with some participants, after one or two of the higher doses, there was a noticeable mental over stimulation. Five of the participants reported no noticeable effects. For other participants, after a few weeks to a month with the higher doses, overstimulation started to occur and was reported by other observers in the household. This effect manifested itself as a noticeable irritability which is described as a “cholinergic” effect of too much choline in the central nervous system. One individual that had been previously consuming up to two grams a day of α-GPC noticed this effect and most treatment-naïve individuals noticed it immediately.

Most interestingly, two elderly individuals (male and female) showed a remarkable response at the high dose level overcoming bland or flat affect and lack of responsiveness characteristic of elderly aging dementia after dosing for a few days. Both individuals showed improvements in short and long term memory as well as in cognitive functions. When these two individuals ran out of the doses, they purchased commercially available market leading product, but did not notice any effect whatsoever. When re-supplied the original high dose the behavior of being enabled to respond and communicate returned. However, after some additional weeks of consumption, the irritability effects of consuming too much choline appeared.

From this ad hoc study, it was determined that acceptable dosing formations for the oral supplements of the present should contain α-GPO at a level of from 25 to 250 mg, disodium phosphocreatine at levels of from 50-500 mg, of an extract containing from 20% to 33% phenolic compounds, of from 25 to 250 mg, and of trisodium citrate from 20 to 50 mg. More preferably, the oral supplements of the present would contain α-GPC at a level of from 60 to 125 mg, disodium phosphocreatine at levels of from 50-500 mg, of an extract containing from 20% to 33% phenolic compounds, of from 50 to 100 mg, and of trisodium citrate from 30 to 60 mg. Most preferably, a dose of the oral dietary supplement of the present invention contains at least 25 mg of polyphenols.

In one preferred form, the oral dietary supplement the present invention comprises disodium phosphocreatine, the plant extract comprises a blueberry extract containing at least 30% total phenols, and a daily dosage of the supplement comprises from 100-350 mg of the α-GPC, 300-750 mg of the disodium phosphocreatine, 100-250 mg of blueberry extract and 0-300 mg trisodium citrate. This supplement and other formulations of the present invention are preferably taken in a form selected from the group consisting of encapsulated powders, tablets, pills, powders, lozenges, elixirs, suspensions, emulsions, solutions, syrups, aerosols, ointments, gelatin capsules and beverages.

Alternatively, a daily dosage of the supplement comprises 250 mg of α-GPO, 500 mg of disodium phosphocreatine, 100 mg of a blueberry extract and 125 mg of the trisodium citrate, and would preferably be incorporated in encapsulated powders, tablets, pills, powders, lozenges, elixirs, suspensions, emulsions, solutions, syrups, aerosols, ointments, gelatin capsules or beverages. Most preferably, the blueberry extract contains at least 30% total phenols.

In other embodiments of oral dietary supplement of the present invention, a daily dosage of the supplement contains from 25-350 mg of α-GPC, 100-750 mg of the disodium phosphocreatine, 25-250 mg of blueberry extract and 0-300 mg trisodium citrate. Preferably, the blueberry extract containing at least 30% total phenols and the supplement is in the form of encapsulated powders, tablets, pills, powders, lozenges, elixirs, suspensions, emulsions, solutions, syrups, aerosols, ointments, gelatin capsules or beverages.

In a particular embodiment of the oral dietary supplement of the present invention, a daily dosage of the supplement comprises 63 mg of the α-GPC, 250 mg of the disodium phosphocreatine, 50 mg of the blueberry extract and 60 mg of the trisodium citrate. Most preferably, the blueberry extract contains least 30% total phenols.

In the most preferred formulations of the present invention, the plant extract enriched in polyphenols comprises a blueberry extract whose bioavailability is enhanced by the presence trisodium citrate. Similarly, the choline component comprises α-GPC whose bioavailability is also enhanced by the presence of the trisodium citrate. Furthermore, the creatine derivative which may comprise disodium phosphocreatine whose bioavailability is also enhanced by the presence of α-GPC, the blueberry extract and the trisodium citrate due to their respective and combined enhanced bioavailability effects.

The invention described herein also includes a method of promoting health of an individual person comprising providing the oral supplements of the present invention to individuals in the combinations described herein, such that improved mental and physical functions might be experienced.

The invention claimed is:

1. An oral dietary supplement comprising:
- approximately 25-250 mg of a plant extract;
- the plant extract enriched in polyphenols;
- the plant extract enriched in polyphenols extracted and selected from the group consisting of polyphenol-containing fruits, fibrous edibles, beans, nuts, spices, teas, vegetables, flowers and grasses;
- the polyphenols selected from the group consisting of monomers, dimers, trimers, oligomers and polymers;
- approximately 50-750 mg of a soluble creatine derivative selected from the group consisting of creatine monohydrate, creatine hydrochloride, disodium phosphocreatine, and creatine phosphate;
- approximately 25-350 mg of a choline derivative selected from the group consisting of alpha-glycerol phosphorylcholine ("α-GPC"), and choline phosphoryl esters; and
- approximately 10-300 mg of a trisodium citrate;
- wherein permeability of at least one of the choline derivative and the plant extract are improved by at least 5% as compared to oral dietary supplements without the trisodium citrate;
- wherein the oral dietary supplement improves at least one of short-term memory, long-term memory, alertness, conversational skills, problem solving, routine personal care, and physical activity.

2. The oral dietary supplement of claim 1 wherein the polyphenols are selected from the group consisting of anthocyanins, phenolic acids, lignans, flavonoids and proanthocyanins.

3. The oral dietary supplement of claim 1 or 2 wherein the plant extract enriched in polyphenols is extracted and selected from the group consisting of acai, aronia, bilberries, blueberries, cranberries, chokeberries, coffee berries, currants, red currents, black currents, black raspberries, elderberries, grapes, mangos, marionberries, peaches, pomegranate, plums, prunes, raspberries and strawberries.

4. The oral dietary supplement of claim 1, wherein the creatine derivative is disodium phosphocreatine.

5. The oral dietary supplement of claim 1, wherein the choline derivative selected is α-GPC.

6. The oral dietary supplement of claim 1, 4, or 5, further comprising an additive selected from the group consisting of alpha-cyclodextrin, a methacrylate copolymer coating, and polyethylene glycol.

7. The oral dietary supplement of claim 1, wherein the creatine derivative comprises creatine phosphate.

8. The oral dietary supplement of claim 1, wherein the creatine derivative comprises creatine hydrochloride; and
- the oral dietary supplement further comprises polyethylene glycol.

9. The oral dietary supplement of claim 1, 4 or 5, wherein the plant extract enriched in polyphenols contains at least 5% of total polyphenols.

10. The oral dietary supplement of claim 1, wherein the creatine derivative comprises disodium phosphocreatine and the plant extract comprises a blueberry extract containing at least 20% total polyphenols.

11. The oral dietary supplement according to claim 1, wherein the supplement is in a form selected from the group consisting of encapsulated powders, tablets, pills, powders, lozenges, elixirs, suspensions, emulsions, solutions, syrups, aerosols, ointments, gelatin capsules and beverages.

12. The oral dietary supplement of claim 1 or 11, wherein the creatine derivative comprises disodium phosphocreatine, the choline derivative comprises α-GPC, the plant extract comprises at least 20% total polyphenols, and the supplement comprises 250 mg of the α-GPC, 500 mg of the disodium phosphocreatine, 100 mg of the blueberry extract and 125 mg of the trisodium citrate.

13. The oral dietary supplement of claim 1 or 11, further comprising magnesium stearate.

14. The oral dietary supplement of claim 1 or 2, wherein the plant extract enriched in polyphenols comprises a blueberry extract, the choline derivative comprises α-GPC, and the creatine derivative comprises disodium phosphocreatine.

15. A method of promoting health of an individual person comprising providing the oral supplement of claim 1, 4, 5, 7 or 8 to the person and administering the oral supplement.

16. The method of promoting health of claim 15 resulting in improved mental and physical functions for the individual consuming the oral supplement.

17. An oral dietary supplement comprising:
- approximately 50 mg of a blueberry extract enriched in polyphenols;
- approximately 250 mg of a disodium phosphocreatine;
- approximately 63 mg of α-GPC; and
- approximately 30-60 mg of a trisodium citrate;
- wherein permeability of at least one of the α-GPC and the blueberry extract are improved by at least 5% as compared to oral dietary supplements without the trisodium citrate;
- wherein the oral dietary supplement improves at least one of short-term memory, long-term memory, alertness, conversational skills, problem solving, routine personal care, and physical activity.

18. The oral dietary supplement of claim 17, wherein the supplement is in a form selected from the group consisting of encapsulated powders, tablets, pills, powders, lozenges, elixirs, suspensions, emulsions, solutions, syrups, aerosols, ointments, gelatin capsules and beverages.

19. The oral dietary supplement of claim 17, wherein the bioavailability of the α-GPC and the blueberry extract is enhanced by the presence of the trisodium citrate.

* * * * *